(12) United States Patent
Kang et al.

(10) Patent No.: US 7,790,889 B2
(45) Date of Patent: Sep. 7, 2010

(54) DI-(4-VINYLPYRIDINE) METAL PHTHALOCYANINE COMPOUND, COMPOSITION COMPRISING THE SAME AND PREPARATION METHOD THEREOF

(75) Inventors: Young Goo Kang, Asan-si (KR); Dae Woo Ihm, Seoul (KR); Shi Surk Kim, Asan-si (KR)

(73) Assignee: Hoseo University Academic Cooperation Foundation (KR)

( * ) Notice: Subject to any disclaimer, the term of this patent is extended or adjusted under 35 U.S.C. 154(b) by 0 days.

(21) Appl. No.: 12/317,402

(22) Filed: Dec. 24, 2008

(65) Prior Publication Data

US 2010/0048902 A1  Feb. 25, 2010

(30) Foreign Application Priority Data

Aug. 20, 2008  (KR) .................... 10-2008-0081146

(51) Int. Cl.
*C07F 15/02* (2006.01)
*F21V 9/16* (2006.01)

(52) U.S. Cl. ............................ 546/2; 252/588; 252/519; 252/8.91

(58) Field of Classification Search ..................... 546/2; 252/519, 588, 8.91

See application file for complete search history.

(56) References Cited

OTHER PUBLICATIONS

Kang, Y.G. et al.: Preparations and antistatic/UV blocking properties of dual functional Phathalocyanine materifals. J. of the KOSOS, vol. 23, pp. 66-71, 2008.

*Primary Examiner*—Charanjit S Aulakh
(74) *Attorney, Agent, or Firm*—Ober/Kaler; Royal W. Craig

(57) ABSTRACT

Disclosed herein are a di-(4-vinylpyridine) metal phthalocyanine compound in which 4-vinylpyridines as ligands are included in a phthalocyanine having a metal, a composition comprising the same and a preparation method thereof. The di-(4-vinylpyridine) metal phthalocyanine compound has an excellent UV blocking effect together with low surface resistance and is prepared but by charging a powder phase with nitrogen, not by dissolving raw materials in an organic solvent as in the prior art.

16 Claims, 2 Drawing Sheets

DI-(4-VINYLPYRIDINE) METAL PHTHALOCYANINE COMPOUND, COMPOSITION COMPRISING THE SAME AND PREPARATION METHOD THEREOF

CROSS-REFERENCE TO RELATED APPLICATION

The present application derives priority from Korean Patent Application No. 10-2008-0081146 filed Aug. 20, 2008, the disclosure of which is incorporated by reference herein in its entirety.

BACKGROUND OF THE INVENTION

1. Field of the Invention

The present invention relates to a phthalocyanine compound, particularly a di-(4-vinylimidazole) metal phthalocyanine compound, a composition comprising the same and a preparation method thereof, and more particularly to a phthalocyanine compound which has an excellent UV (Ultraviolet)-blocking effect together with low surface resistance and is prepared by charging a powder phase with nitrogen, not by dissolving raw materials in an organic solvent as in the prior art.

2. Description of the Background

A phthalocyanine is a macrocyclic compound having an alternating nitrogen atom-carbon atom ring structure. Recently, phthalocyanine compounds have been widely used in various fields, because they have high visible light transmittance and a high infrared ray shielding effects, are excellent in the ability to selectively filter light, particularly in the near infrared region, and show excellent heat resistance, light resistance and weather resistance.

For example, Korean Patent Laid-Open Publication No. 2003-96052 discloses a phthalocyanine compound represented by the following Formula 1, which can be advantageously used for plasma display front panels:

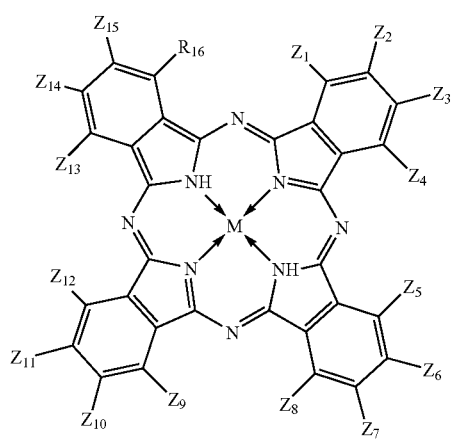

[Formula 1]

where, $Z_2$, $Z_3$, $Z_6$, $Z_7$, $Z_{10}$, $Z_{11}$, $Z_{14}$ and $Z_{15}$ each represents $SR_1$, $SR_2$, $OR_3$ or a halogen atom, provided that at least one thereof represents $SR_2$; and $Z_1$, $Z_4$, $Z_5$, $Z_8$, $Z_9$, $Z_{12}$, $Z_{13}$ and $Z_{16}$, each represents NHR4, NHR5, SR1, SR2, OR3 or a halogen atom, provided that at least one thereof represents NHR5 and that at least four thereof represent OR3; wherein R1 represents an optionally substituted phenyl group, an alkyl group or an optionally substituted C1-C20 alkyl group; R2 represents a phenyl group optionally substituted with a C1-C20 alkoxy group; R3 and R4 each represent an optionally substituted phenyl group, an alkyl group or an optionally substituted C1-C20 alkyl group; R5 represents an optionally substituted C1-C20 alkyl group; R1, R2, R3, R4 and R5 may be the same or different from each other; and M represents a non-metal, a metal, a metal oxide or a metal halide.

The phthalocyanine compounds having the above-described structure can be easily obtained by adding phthalic anhydride, phthalimide, dicyanobenzene, 1,2-dicyanoisoindoline or the like to urea and a metal and allowing the mixture to react at high temperature while blocking the introduction of oxygen during the reaction or using a high-boiling-point solvent.

However, such phthalocyanine compounds have problems in that they have high surface resistance, are used as a near infrared light absorber in a limited wavelength region and show low light absorptivity. In addition, such phthalocyanine compounds have problems in that they have a relatively low reactivity and a low solubility in a solvent, and thus are prepared in low yield. Furthermore, they show low coating efficiency when being used to prepare films and, in addition, do not show sufficient reactivity in a gelling process.

SUMMARY OF THE INVENTION

Therefore, it is an object of the present invention to provide a metal phthalocyanine compound which has a surface resistance of a predetermined level $10^{11}$ $\Omega/cm^2$ or below, and thus can be advantageously used to prepare an antistatic layer.

Another object of the present invention is to provide a metal phthalocyanine compound having an excellent ultraviolet (UV) blocking effect and a film comprising the same.

Still another object of the present invention is to prepare a phthalocyanine compound through a novel method of attaching ligands by charging a powder phase in a closed vessel with nitrogen, not by dissolving raw materials in an organic solvent.

To achieve the above objects, in one aspect, the present invention provides a di-(4-vinylpyridine) metal phthalocyanine compound having a structure of the following formula 2:

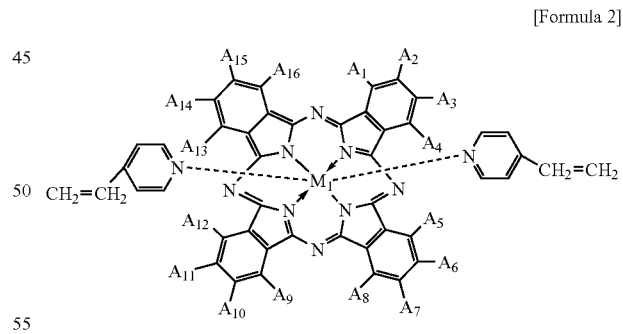

[Formula 2]

where $M_1$ is an iron, cobalt or ruthenium metal; $A_1$ to $A_{16}$ may be the same or different, each representing a hydrogen atom, a halogen atom, a hydroxyl group, an amino group, a hydroxysulfonyl group, an aminosulfonyl group, an alkyl group, a substituted C1-C20 alkyl group, SA17, SA18, OA19, NHA20 or NHA21; wherein A17 is a substituted phenyl, an alkyl group or a C1-C20 alkyl group; A18 is a phenyl group substituted with a C1-C20 alkoxy group, A19 and A20 each represents a substituted phenyl, an arylalkyl group or a C1-C20 alkyl group; and A21 is a substituted C1-C20 alkyl group.

Another aspect of the present invention may be an antistatic composition, an UV-absorbing composition and an antistatic and UV-absorbing composition, which comprise the di-(4-vinylpyridine) metal phthalocyanine compound as described above.

Still another aspect of the present invention is a method for preparing a di-(4-vinylpyridine) metal phthalocyanine compound, the method comprising the steps of: 1) charging a mixed powder of metal phthalocyanine powder and 4-vinylpyridine with nitrogen; and then stirring the mixture; and washing the stirred reaction product, drying the washed powder, and then purifying the dried powder.

Other features and aspects of the present invention will be more apparent from the following detailed description and the accompanying drawings.

According to the present invention, there may be provided a metal phthalocyanine compound in which 4-vinylpyridien as a ligand is included in a phthalocyanine having a metal. This compound may be advantageously used to prepare an antistatic layer having a surface resistance of a given level or below.

Moreover, the metal phthalocyanine compound according to the present invention has an excellent UV-blocking effect, and thus may be provided as an UV-blocking film.

In addition, according to the present invention, a phthalocyanine compound may be prepared through a novel method of attaching ligands by charging a powder phase in a closed vessel with nitrogen, not by dissolving raw materials in an organic solvent.

DETAILED DESCRIPTION

Figure 1:
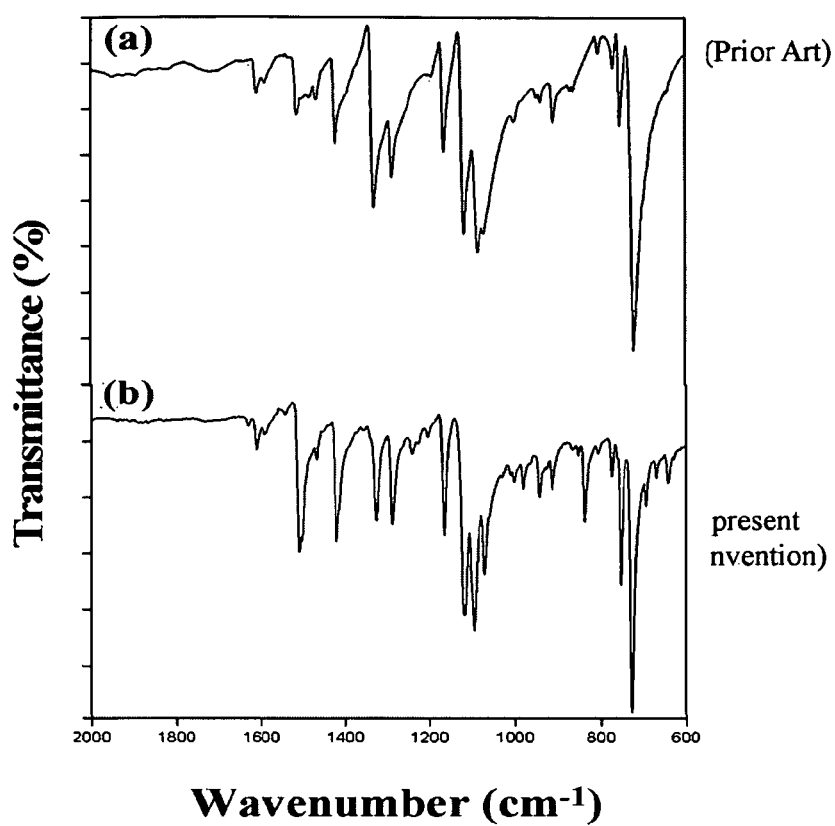
FIG. 1 is a graphic diagram showing the ATR-FTIR spectra of single-molecule-type iron phthalocyanine (a) according to the prior art and a di-(4-vinylpyridine) iron phthalocyanine compound (b) according to a preferred embodiment of the present invention.

Hereinafter, a preferred embodiment of the present invention will be described in detail with the accompanying drawings.

A To achieve the above objects, in one aspect, the present invention provides a di-(4-vinylpyridine) metal phthalocyanine compound having a general structure of the following Formula 2:

[Formula 2]

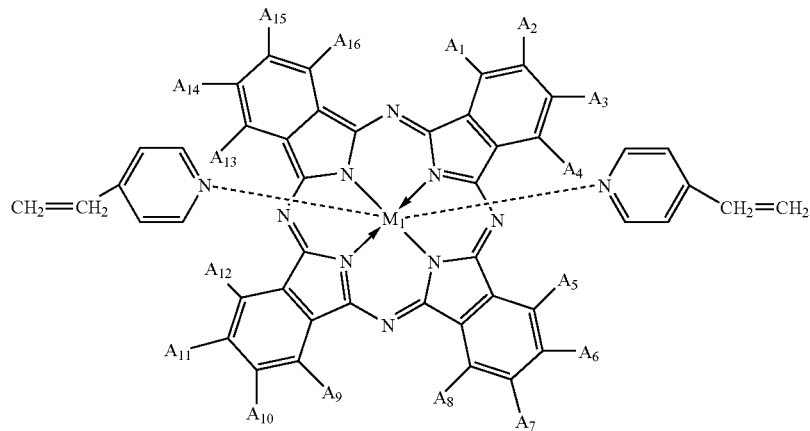

where, $M_1$ is an iron, cobalt or ruthenium metal; $A_1$ to $A_{16}$ may be the same or different, each individually representing a hydrogen atom, a halogen atom, a hydroxyl group, an amino group, a hydroxysulfonyl group, an aminosulfonyl group, an alkyl group, a substituted C1-C20 alkyl group, SA17, SA18, OA19, NHA20 or NHA21; wherein A17 is a substituted phenyl, an alkyl group or a C1-C20 alkyl group; A18 is a phenyl group substituted with a C1-C20 alkoxy group; A19 and A20 each represents a substituted phenyl, an arylalkyl group or a C1-C20 alkyl group; and A21 is a substituted C1-C20 alkyl group.

This single-molecule-type phthalocyanine compound of the present invention has a metal in the center thereof, includes two 4-vinylpyridines, and thus has a surface resistance of a predetermined level $10^{11}$ $\Omega/cm^2$ or below. Accordingly, the compound of the present invention can be advantageously used as a composition for preparing either an antistatic layer or an antistatic film comprising the same.

Such changes can be readily observed through the measurement and analysis of surface resistance. Specifically, a film coated with the di-(4-vinylpyridine) metal phthalocyanine compound according to the present invention had a surface resistance of less than $10^{11}$ $\Omega/cm^2$, whereas a virgin polyester film not coated with the compound showed a surface resistance of about $10^{16}$ $\Omega/cm^2$. Accordingly, the present invention may be a di-(4-vinylpyridine) metal phthalocyanine compound for preventing static electricity or a composition comprising the same.

Also, the di-(4-vinylpyridine) metal phthalocyanine compound has excellent UV-blocking effects, and such effects can be readily seen from the results of spectrophotometric analysis. Specifically, general commercial phthalocyanine compounds show light absorbance in the visible light region at about 670 nm, whereas the di-(4-vinylpyridine) metal phthalocyanine compound according to the present invention and a film coated therewith have absorption wavelengths in the UV region at about 200-350 nm. It seems that the di-(4-vinylpyridine) metal phthalocyanine compound has a structure in which it has a metal in the center thereof, and two 4-vinylpyridines as ligands are bound thereto, and due to this structural difference, the compound of the present invention shows an absorbance region different from that of the single-molecule-type phthalocyanine according to the prior art.

For this reason, the di-(4-vinylpyridine) metal phthalocyanine compound according to the present invention has an excellent ability to absorb UV light, and thus can be advantageously used as a composition for either a UV blocking layer or a UV blocking film comprising the same. Accordingly, the present invention may be a di-(4-vinylpyridine) metal phthalocyanine compound for blocking UV light or a composition comprising the same.

In the present invention, a compound is prepared in which axial functional ligands are introduced into the central axis of the prior phthalocyanine compound according to an axial reaction, particularly in which two 4-vinylpyridines are introduced as ligands. As described above, the compound according to the present invention has low surface resistance together with an excellent UV-blocking effect. Furthermore, the compound of the present invention has increased solubility in solvents, and thus can be prepared in high yield. In addition, it has high coating efficiency when being used to form a film and may have high applicability in a gelling process.

According to a preferred embodiment of the present invention, the di-(4-vinylpyridine) metal phthalocyanine compound having the general structure of Formula 2 may be specifically represented by the following Formula 3, wherein any one of $A_1$ to $A_4$, $A_5$ to $A_8$, $A_9$ to $A_{12}$ and $A_{13}$ to $A_{16}$ is R and the remainder is hydrogen. Specifically, any one of $A_1$ to $A_4$ is R and the remainder is hydrogen, any one of $A_5$ to $A_8$ is R and the remainder is hydrogen, any one of $A_9$ to $A_{12}$ is R and the remainder is hydrogen, and any one of $A_{13}$ to $A_{16}$ is R and the remainder is hydrogen.

where, $M_1$ is an iron, cobalt or ruthenium metal; and R is hydrogen or at least one functional group or substituent. R in Formula 3 is preferably a hydrogen atom, a halogen atom or a C1-C20 alkyl group, but preferably hydrogen.

Meanwhile, another aspect of the present invention relates to a method for preparing the di-(4-vinylpyridine) metal phthalocyanine compound as described above, the method comprising the steps of: 1) charging a mixed powder of metal phthalocyanine powder and 4-vinylpyridine powder with nitrogen, and then stirring the mixture; and 2) washing the stirred reaction product, drying the washed powder, and then purifying the dried powder.

This method of the present invention is a novel method of attaching ligands by charging powdery raw materials in a closed vessel with nitrogen, not by dissolving raw materials in an organic solvent as in the prior art. Namely, an existing commercial phthalocyanine compound is prepared by dissolving phthalocyanine in an organic solvent, and then mixing the solution with other materials, whereas the di-(4-vinylpyridine) metal phthalocyanine compound according to the present invention can be prepared using a novel method of melting phthalocyanine and 4-vinylpyridine in a closed vessel without dissolving them in a separate inorganic solvent. According to the method of the present invention, the risk of explosion and generation of noxious vapor according to the use of an organic solvent can be avoided, unlike general methods for preparing organic compounds.

In the present invention, the mixing ratio between metal phthalocyanine powder and 1-vinylpyridine powder in the mixed powder is preferably in the range from 1:20 parts by weight to 1:40 parts by weight. If the mixing ratio is lower than the lower limit of the specified range, 4-vinylpyridine as a ligand cannot be sufficiently bound to the metal, and if it is higher than the upper limit of the specified range, an unnecessarily large amount of 4-vinylpyridine will be used in a preparation process.

The present invention will be more readily understood with reference to the following examples, and it is to be understood, however, that these examples are illustrative only and are not construed to limit the scope of the present invention as defined by the appended claims.

As used herein, the term "metal phthalocyanine compound" refers to a compound in which a metal is included in the center of a single-molecule-type phthalocyanine. The metal, iron (Fe) is described herein by way of the following

[Formula 3]

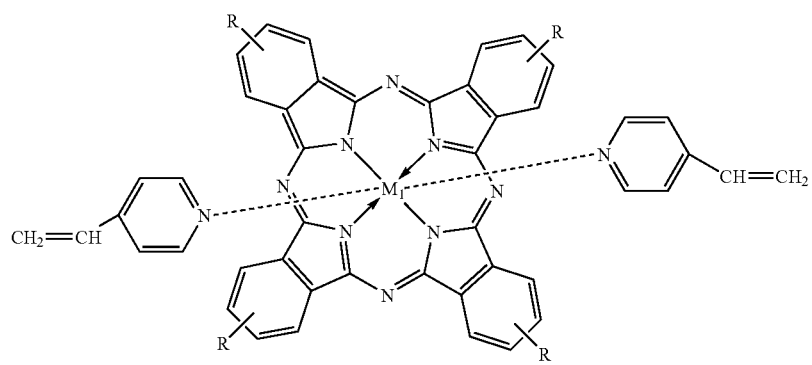

examples, but it should be obvious to one skilled in the art that other metals in addition to iron may be included. Thus, the iron phthalocyanine compounds of the present invention also include those having other metals in addition to iron.

Example 1

Preparation of di-(4-vinylpyridine) Iron Phthalocyanine Compound

In order to prepare a di-(4-vinylpyridine) iron phthalocyanine compound according to the present invention, powdery iron phthalocyanine (available from Sigma-Aldrich™) was sublimed in a vacuum at a pressure of $10^{-6}$ torr and a temperature of 260° C. to remove impurities, and powdery 4-vinylpyridine (4-VP, Aldrich) was distilled under reduced pressure before use. 1 part by weight of the above-purified iron phthalocyanine and 30 parts by weight of the distilled 4-vinylpyridine were sufficiently mixed with each other in a closed vessel, and then the vessel was charged with nitrogen and sealed. Then, the mixture was stirred at 110° C. for 12 hours. The stirred reaction product was washed with methanol, until the color of the washing solution disappeared. Then, the washed powder was dried at 70° C. for 24 hours, and 1 part by weight of the dried powder was dissolved in 30 parts by weight of dichloromethane ($CH_2Cl_2$). The dissolved fraction was purified by passing it through a $SiO_2$ (neutral) column. Then, the purified material was dried in a vacuum of $10^{-3}$ torr at a temperature of 70° C. for 12 hours, thus obtaining a di-(4-vinylpyridine) iron phthalocyanine compound according to the present invention.

The di-(4-vinylpyridine) iron phthalocyanine compound thus prepared was a compound in which $M_1$ in the above formula 3 is an iron metal and R is a hydrogen atom.

Test Example 1

Analysis of Structure of di-(4-vinylpyridine) Iron Phthalocyanine Compound

FIG. 1 is a graphic diagram showing the ATR-FTIR spectra of a single-molecule-type iron phthalocyanine (a) according to the prior art and a di-(4-vinylpyridine) iron phthalocyanine [$PcFe(4-VP)_2$] compound (b) according to a preferred embodiment of the present invention.

As can be seen from the graphic diagram of FIG. 1 showing ATR-FTIR spectra, the single-molecule-type iron phthalocyanine according to the prior art and the di-(4-vinylpyridine) iron phthalocyanine compound according to the present invention were similar to each other with respect to whole wavelength and showed a fine difference ($cm^{-1}$) in intrinsic wavelength.

Namely, the two wavelengths in (a) and (b) of FIG. 1 showed the base peaks at 725, 752 773, 912, 1070, 1094, 1116, 1164, 1288, 1326, 1420 and 1610 $cm^{-1}$, suggesting that the prior iron phthalocyanine and the di-(4-vinylpyridine) iron phthalocyanine had very similar phthalocyanine structures. Particularly, the di-(4-vinylpyridine) iron phthalocyanine according to the present invention showed new peaks at 837, 980, 1240 and 1502 $cm^{-1}$ compared to the prior iron phthalocyanine, and it was analyzed that these new peaks were shown because di-(4-vinylpyridines) were introduced as ligands by axial ligand reactions according to the present invention.

Test Example 2

Figure 2:
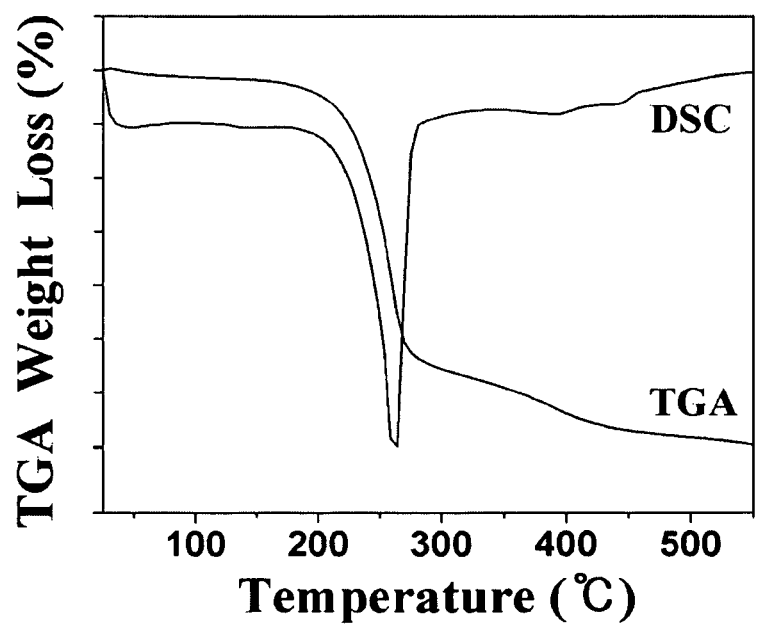
FIG. 2 is a graphic diagram showing the date of thermal analysis (Thermo Gravimetric Analysis or TGA, and differential scanning calorimeter or DSC) of a di-(4-vinylpyridine) iron phthalocyanine compound according to a preferred embodiment of the present invention.

Results of Thermal Analysis of di-(4-vinylpyridine) Iron Phthalocyanine Compound FIG. 2 is a graphic diagram showing the data of thermal analysis (TGA and DSC) of the di-(4-vinylpyridine) iron phthalocyanine compound according to the preferred embodiment of the present invention. Such thermal analysis enables the heat resistance (DSC) and structure (TGA weight loss) of the inventive compound to be seen.

Specifically, as can be seen from the DSC graph of FIG. 2, the di-(4-vinylpyridine) iron phthalocyanine compound started to show a fine change in temperature at about 156° C., and this was thought to be resulted from the fact that the decomposition of 4-vinylpyridine as a ligand in the compound of the present invention was initiated at that temperature. Accordingly, it can be seen that, because the di-(4-vinylpyridine) iron phthalocyanine compound of the present invention starts to be decomposed at about 156° C., it has sufficient heat resistance up to a relatively high temperature of 150° C.

Theoretically, the weight loss ratio corresponding to a theoretical value of 2 moles of 1-vinylpyridine for the di-(4-vinylpyridine) iron phthalocyanine compound according to the present invention upon the decomposition of the compound is calculated to be 27%. As can be seen in the TGA graph of FIG. 2, the inventive compound prepared in Example 1 showed a weight loss ratio of 26.3% which was significantly consistent with the theoretically calculated value. This confirms again that the di-(4-vinylpyridine) iron phthalocyanine compound according to the present invention includes two 4-vinylpyridines as ligands.

Test Example 3

Analysis of UV spectrum of di-(4-vinylpyridine) Iron Phthalocyanine Compound

Figure 3:
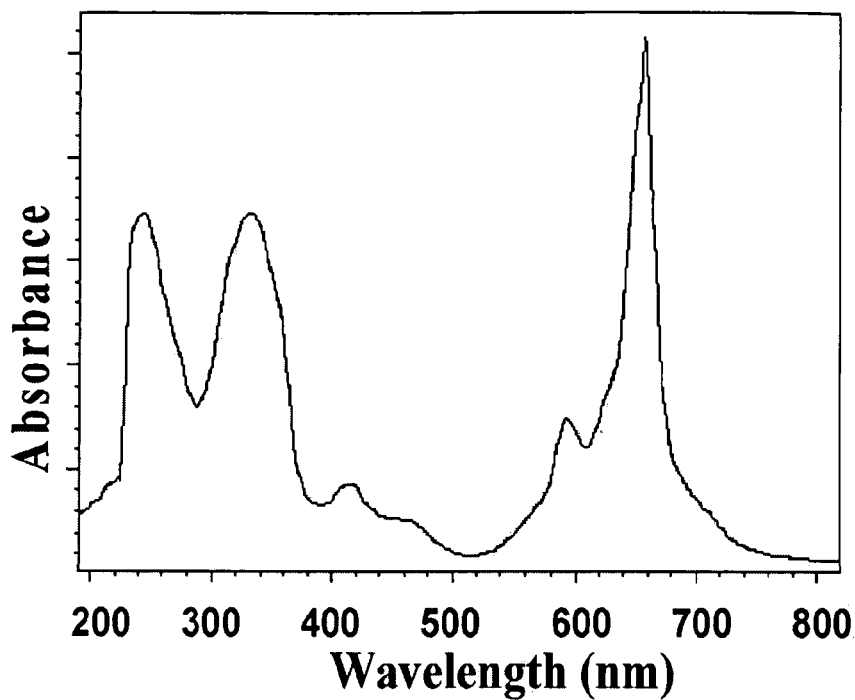
FIG. 3 is a graphic diagram showing the UV-Vis spectrum of a di-(4-vinylpyridine) iron phthalocyanine compound dissolved in dichloromethane ($CH_2Cl_2$) according to a preferred embodiment of the present invention.

FIG. 3 is a graphic diagram showing the UV-Vis spectrum of the di-(4-vinylpyridine) iron phthalocyanine compound dissolved in dichloromethane ($CH_2Cl_2$) according to an embodiment of the present invention. This shows the UV absorptivity of the di-(4-vinylpyridine) iron phthalocyanine compound itself.

As shown therein, the di-(4-vinylpyridine) iron phthalocyanine compound dissolved in the $CH_2Cl_2$ solvent showed the Q-band at 656 nm and the B-band at 332 nm. Accordingly, it can be seen that the compound according to the present invention has excellent UV absorptivity, because it shows the Q-band at 656 nm and the B-band at 332 nm.

Example 2

Preparation of Film Coated with di-(4-vinylpyridine) Iron Phthalocyanine

A film coated with the di-(4-vinylpyridine) iron phthalocyanine compound according to the present invention was prepared.

Specifically, 6 g of a pigment consisting of the di-(4-vinylpyridine) iron phthalocyanine compound [$PcFe(4-VP)_2$] obtained in Example 1 was dispersed in dichloromethane (Aldrich), and 30 g of polyurethane resin (UA 7008WR, Aekyung Chemical Co., Ltd.) was added thereto. Then, the mixture was dispersed with a 3-roll mill, thus preparing an ink composition for film coating.

The prepared ink composition for film coating was coated on a polyester film (Virgin PET) to a thickness of 30☐, and then dried at 120° C. for 1 hour, thus obtaining a film.

Test Example 4

Measurement of Surface Resistance and UV Absorptivity of Film Coated with di-(4-vinylpyridine) Iron Phthalocyanine Compound Using a surface resistance meter (Monroe, 262A), the surface resistance of each of the film prepared in Example 2 and a general polyester film (Virgin PET) was measured.

The present inventors found that the general virgin PET film showed a surface resistance of less than $10^{16}$ $\Omega/cm^2$, whereas the film prepared in Example 2 showed a surface resistance of less than $10^{11}$ $\Omega/cm^2$. Accordingly, it can be seen that the film coated with the di-(4-vinylpyridine) iron phthalocyanine compound according to the present invention can be used as an antistatic film having low surface resistance.

Figure 4:
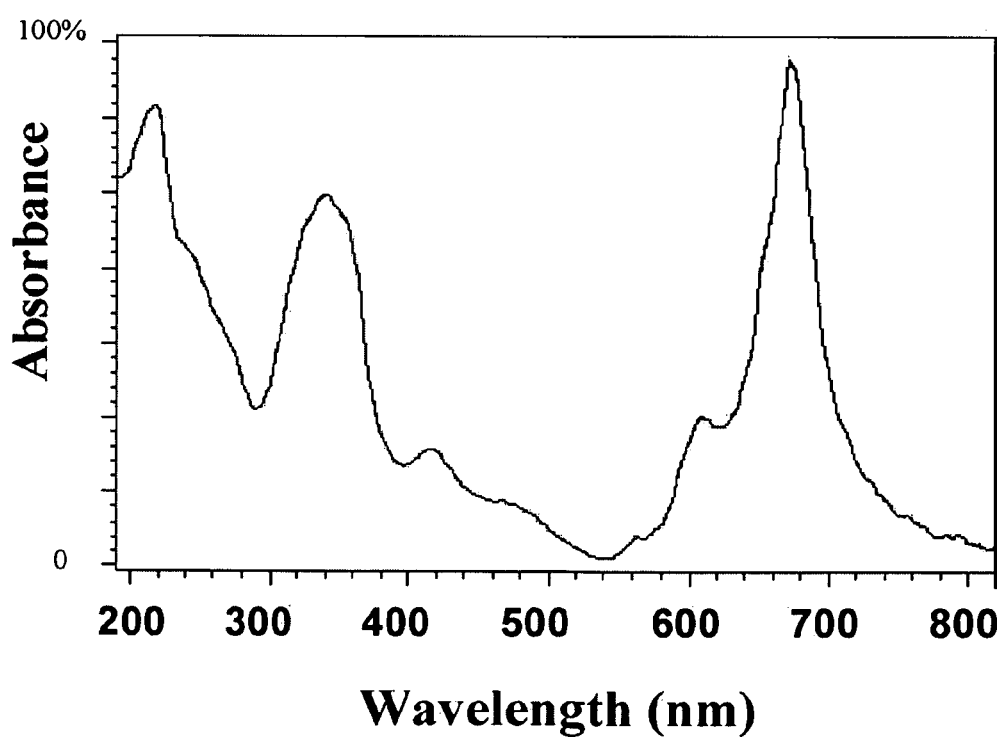
FIG. 4 is a graphic diagram showing the UV-Vis spectrum of a di-(4-vinylpyridine) iron phthalocyanine compound coated on a film according to a preferred embodiment of the present invention.

Meanwhile, FIG. 4 is a graphic diagram showing the UV-Vis spectrum of the di-(4-vinylpyridine) iron phthalocyanine coated on a film according to the present invention.

In order to examine the UV/Vis absorbing properties of the di-(4-vinylpyridine) iron phthalocyanine compound according to the present invention, the di-(4-vinylpyridine) iron phthalocyanine compound [PcFe(4-VP)$_2$] prepared in Example 1 was coated on a quartz plate, and then dried, thus preparing a film. Measurement results for the UV/Vis spectrum of the film are shown in Table 1 below.

TABLE 1

Test results for UV-Vis absorbance wavelength

| Test Examples | Compounds | Bands | Remarks |
|---|---|---|---|
| Test Example 3 | di-(4-vinylpyridine) iron phthalocyanine compound | 244, 332, 414, 464(sh), 594 and 656 nm | CH$_2$Cl$_2$ |
| Test Example 4 | di-(4-vinylpyridine) iron phthalocyanine compound | 218, 340, 418, 466(sh), 610 and 672 nm | Film |

As can be seen in FIG. 4 and Table 1, the film coated with the di-(4-vinylpyridine) iron phthalocyanine compound according to the present invention has high UV absorptivity at 218 nm and 340 nm which are intrinsic wavelengths, suggesting that the film can be advantageously used as a film having a UV blocking effect. In comparison with the UV blocking effect of the di-(4-vinylpyridine) iron phthalocyanine compound itself as measured in Test Example 3, the dried film prepared using the compound showed a shift in the Q-band from 656 nm to 678 nm (that is, a shift to the long-wavelength side by 16 nm) and a shift in the B-band from 234 nm to 220 nm (shift to the short-wavelength side), suggesting that the film prepared using the compound has a more excellent UV-blocking effect.

As described above, the present invention can provide an iron phthalocyanine compound having a surface resistance of a given level or below together with an excellent UV-blocking effect and provide a film prepared using the same.

Although the preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A di-(4-vinylpyridine) metal phthalocyanine compound having a structure of the following formula 2:

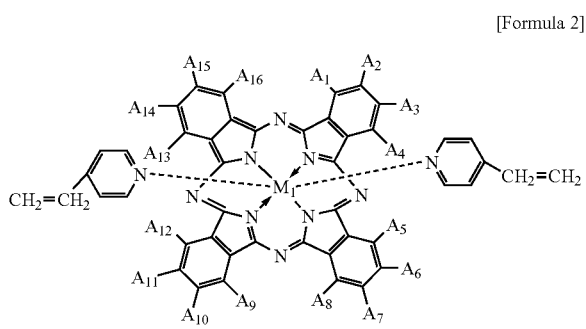

[Formula 2]

where, M$_1$ is an iron, cobalt or ruthenium metal, A$_1$ to A$_{16}$ may be the same or different, each representing a hydrogen atom, a halogen atom, a hydroxyl group, an amino group, a hydroxysulfonyl group, an aminosulfonyl group, an alkyl group, SA17, SA18, OA19, NHA20 or NHA21, wherein A17 is a substituted phenyl or an alkyl group, A18 is a phenyl group substituted with a C1-C20 alkoxy group, A19 and A20 each represents a substituted phenyl, an arylalkyl group or a C1-C20 alkyl group, and A21 is a substituted C1-C20 alkyl group.

2. The di-(4-vinylpyridine) metal phthalocyanine compound of claim 1, wherein the compound of formula 2 is represented by the following formula 3:

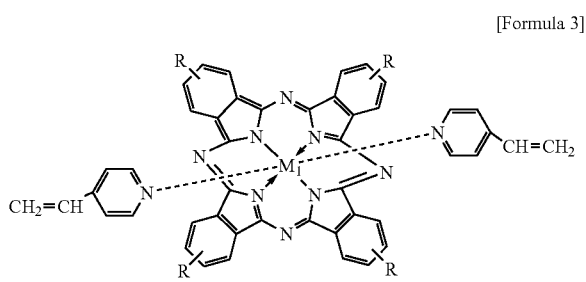

[Formula 3]

where M$_1$ is an iron, cobalt or ruthenium metal, and R is a hydrogen atom, a halogen atom or a C-1-C-20 alkyl group.

3. The di-(4-vinylpyridine) metal phthalocyanine compound of claim 2, where R in Formula 3 comprises hydrogen.

4. An antistatic composition comprising the di-(4-vinylpyridine) metal phthalocyanine compound as set forth in claim 1.

5. An antistatic composition comprising the di-(4-vinylpyridine) metal phthalocyanine compound as set forth in claim 2.

6. An antistatic composition comprising the di-(4-vinylpyridine) metal phthalocyanine compound as set forth in claim 3.

7. An ultraviolet UV light absorbing composition comprising the di-(4-vinylpyridine) metal phthalocyanine compound as set forth in claim 1.

8. A UV absorbing composition comprising the di-(4-vinylpyridine) metal phthalocyanine compound as set forth in claim 2.

9. A UV absorbing composition comprising the di-(4-vinylpyridine) metal phthalocyanine compound as set forth in claim 3.

10. An antistatic and UV absorbing composition comprising the di-(4-vinylpyridine) metal phthalocyanine compound as set forth in claim 1.

11. An antistatic and UV absorbing composition comprising the di-(4-vinylpyridine) metal phthalocyanine compound as set forth in claim 2.

12. An antistatic and UV absorbing composition comprising the di-(4-vinylpyridine) metal phthalocyanine compound as set forth in claim 3.

13. A method for preparing a di-(4-vinylpyridine) metal phthalocyanine compound as claimed in claim 1, the method comprising the steps of:

charging a mixed powder of metal phthalocyanine powder and 4-vinylpyridine powder with nitrogen and stirring the powder mixture; and washing the stirred powder mixture, drying the washed powder, and then purifying the dried powder.

14. The method of claim 13, wherein the mixing ratio between the metal phthalocyanine powder and the 4-vinylpyridine powder in the mixed powder is in the range from 1:20 parts by weight to 1:40 parts by weight.

15. The method of claim 13, wherein said step of charging a mixed powder of metal phthalocyanine and 4-vinylpyridine powder with nitrogen is accomplished in a closed vessel.

16. The method of claim 13, wherein said step of charging a mixed powder of metal phthalocyanine and 4-vinylpyridine powder with nitrogen in a closed vessel attaches ligands.

* * * * *